United States Patent [19]

Green et al.

[11] 4,005,193

[45] * Jan. 25, 1977

[54] MICROBIOCIDAL POLYMERIC QUATERNARY AMMONIUM COMPOUNDS

[75] Inventors: Harold A. Green, Havertown, Pa.; John J. Merianos, Jersey City; Alfonso N. Petrocci, Glen Rock, both of N.J.

[73] Assignee: Millmaster Onyx Corporation, New York, N.Y.

[ * ] Notice: The portion of the term of this patent subsequent to Apr. 1, 1992, has been disclaimed.

[22] Filed: Oct. 20, 1975

[21] Appl. No.: 623,750

Related U.S. Application Data

[63] Continuation-in-part of Ser. No. 495,328, Aug. 7, 1974, Pat. No. 3,929,990, which is a continuation-in-part of Ser. No. 425,931, Dec. 18, 1973, Pat. No. 3,874,870.

[52] U.S. Cl. .................................. 424/168; 424/78; 424/329

[51] Int. Cl.² ..................... A01N 9/04; A01N 9/20; A01N 9/24; A01N 17/10

[58] Field of Search ............ 424/168, 329, 325, 78

[56] References Cited

UNITED STATES PATENTS

| | | | |
|---|---|---|---|
| 3,140,976 | 7/1964 | Berenschot et al. | 424/329 |
| 3,296,145 | 1/1967 | Findlan et al. | 252/106 |
| 3,539,684 | 11/1970 | Hoover | 424/78 |
| 3,771,989 | 11/1973 | Pera et al. | 424/329 |
| 3,778,283 | 12/1973 | Freyhold | 106/84 |
| 3,929,990 | 12/1975 | Green et al. | 424/329 |

*Primary Examiner*—Albert T. Meyers
*Assistant Examiner*—D. W. Robinson
*Attorney, Agent, or Firm*—Arthur A. Jacobs

[57] ABSTRACT

Water-in-oil emulsions containing a polymeric quaternary ammonium compound prepared by the condensation of 1,4-dihalo-2-butene and 1,4-bis-dimethylamino-2-butene as a biocidal agent, and wherein the emulsifying agent is an amine oxide.

3 Claims, No Drawings

MICROBIOCIDAL POLYMERIC QUATERNARY AMMONIUM COMPOUNDS

This is a continuation-in-part of application Ser. No. 495,328, filed Aug. 7, 1974 and issued as U.S. Pat. No. 3,929,990, dated Dec. 30, 1975, which was, in turn, a continuation-in-part of application Ser. No. 425,931, filed Dec. 18, 1973, now issued as U.S. Pat. No. 3,874,870, dated Apr. 1, 1975.

This invention relates to water-in-oil emulsions which contain a polymeric quaternary ammonium compound as a anti-fungal agent, and it particularly relates to such emulsions wherein the emulsifying agent is an amine oxide.

The aforesaid application Ser. No. 425,931, disclosed that the polymeric quaternary ammonium compound formed by the condensation of 1,4-dihalo-2-butene and 1,4-bis-dimethylamino-2-butene comprises a very potent biocidal agent in oil-in-water emulsions and that such emulsions have relatively little foaming action.

As disclosed in the aforesaid application Ser. No. 425,931, which is herewith incorporated by reference, the aforesaid polymeric quaternary ammonium compound is formed by mixing 1,4-dihalo-2-butene and 1,4-bis-dimethylamino-2-butene dissolved in a solvent, in relative molar proportions of between about 1:3 and about 3:1, at room temperature, whereby an exothermic reaction is obtained causing the temperature of the mixture to rise, then maintaining the mixture at no higher than reflux temperature until the reaction is complete. For the sake of brevity, this compound will be referred to as "Product P".

This same polymeric quaternary ammonium compound provides the same satisfactory results when used in water-in-oil emulsions, except when such water-in-oil emulsions include non-ionic emulsifiers. When such non-ionic emulsifiers are present, biocidal effectiveness is seriously impaired. However, when the non-ionic emulsifier is replaced by an amine oxide as the emulsifying agent, the biocidal effectiveness is satisfactory.

In the same manner as the oil-in-water emulsions described in the aforesaid parent application, the compound in the present water-in-oil emulsions is active at concentrations as low as 10 ppm against Aerobacter aerogenes and as low as 25 ppm against Pseudomonas aeruginosa, while against algae, such as *Chlorella pyrenoidosa*, it is active at a concentration at least as low as 1 ppm or lower, and it is active against a mixture of the fungi *Aspergillis niger* and *Penicillium expansum* in concentrations of about 2000 ppm, or less, as a inhibitor against proliferation. Insofar as concerns their upper limits, the concentration appears to be capable of being increased indefinitely without deleteriously affecting the biocidal activity.

Also, as in the case of the corresponding oil-in-water emulsions described in the aforesaid parent application, when used in cosmetic compositions the present water-in-oil emulsions are effectively protected by the polyquaternary compound.

In order to show anti-fungal activity of water-in-oil emulsions, utilizing the present polymeric quaternary ammonium compound, wherein an amine oxide is used as the emulsifying agent, a cosmetic-type water-in-oil emulsion was prepared using an emulsion containing an amine oxide, namely "Ammonyx SO", as the emulsifier. "Ammonyx SO" is stearyldimethylamine-N-oxide made by the Onyx Chemical Company, Jersey City, N.J.

The amine oxide, "Ammonyx SO" is dissolved in water, together with "Product P", at 65° to 75° C. Then, the lanolin, petrolatum and mineral oil are heated to a homogeneous melt at between 65° to 75° C. Thereafter, with constant mechanical stirring, the aqueous phase is added very slowly to the oil phase and stirring is continued while cooling, until a stable smooth emulsion results.

The following tables illustrate the particular compositions used and the anti-fungal results achieved with each composition:

Table 1

The following emulsions were prepared for microbiological testing:

|  | Emulsion A | Emulsion B | Emulsion C |
|---|---|---|---|
| Lanolin, USP Anhydrous | 2.0 | 2.0 | 2.0 |
| Mineral oil (65/76 saybolt) | 40.0 | 40.0 | 40.0 |
| Petrolatum, White USP | 30.0 | 30.0 | 30.0 |
| "Ammonyx SO" (25%) | 16.0 | 16.0 | 16.0 |
| "Product P" | 1.0 | 0.5 | 0.2 |
| Water | 11.0 | 11.5 | 11.8 |

|  | Emulsion D | Emulsion E |
|---|---|---|
| Lanolin, USP Anhydrous | 2.0 | 1.0 |
| Mineral oil (65/75 saybolt) | 40.0 | 35.0 |
| Petrolatum, White USP | 30.0 |  |
| "Ammonyx SO" | 16.0 | 10.0 |
| "Product P" | 0.0 | 0.2 |
| Cetyl Alcohol |  | 1.0 |
| Water | 12.0 | 52.8 |

Emulsions A, B, C and D are water-in-oil emulsions containing "Product P" in concentrations of 10,000 ppm; 5,000 ppm; 2,000 ppm; and 0 ppm respectively.

Emulsion E is an oil-in-water emulsion of "Product P", which has been shown to be a potent fungicidal emulsion.

Emulsion D is a "negative" control for emulsions A, B, C and emulsion E is a "positive" control for emulsions A, B, and C.

Following is a description of the method used in testing for the anti-fungal properties of water-in-oil emulsions.

Fifty gram samples of each emulsion to be tested were aseptically transferred to sterile 8 ounce widemouth jars. Two replicate jars and an untreated control were prepared in each instance.

Each jar was inoculated with 5.0 ml. of an aqueous suspension of *Aspergillis niger*, and *Penicillium expansum* to provide a concentration of $1 \times 10^5$ spores per ml. of jar content. (The spore suspension was prepared previously as an aqueous suspension of 14 day old agar growth of test organisms).

At weekly intervals following inoculation, some of the jar contents in sterile "Azolectin"-"Tween 80" sterile neutralizer solutions were plated into Sabouraud Dextrose agar, incubated at 28° C, and observed at 7 and 14 days following the plating, to count the number of colonies arising from the viable spores.

Table 2

|  | Number of Spores Counted | | | | |
|---|---|---|---|---|---|
|  | Start | Week 1 | Week 2 | Week 3 | Week 4 |
| Emulsion A | $1 \times 10^5$ | $2 \times 10^3$ | $16 \times 10^1$ | $8 \times 10^1$ | $6 \times 10^1$ |
| Emulsion B | $1 \times 10^5$ | $5 \times 10^3$ | $42 \times 10^1$ | $64 \times 10^1$ | $45 \times 10^1$ |
| Emulsion C | $1 \times 10^5$ | $9 \times 10^3$ | $63 \times 10^1$ | $86 \times 10^1$ | $14 \times 10^1$ |
| Emulsion D | $1 \times 10^5$ | $2 \times 10^5$ | $34 \times 10^4$ | $13 \times 10^4$ | $18 \times 10^4$ |

Table 2-continued

| | Number of Spores Counted | | | | |
|---|---|---|---|---|---|
| | Start | Week 1 | Week 2 | Week 3 | Week 4 |
| Emulsion E | $1 \times 10^5$ | <10 | <10 | <10 | <10 |

The biocidal test results displayed in Tables 1 and 2 clearly indicate that the polyquaternary compound functions as an effective anti-fungal agent in water-in-oil emulsions when it is in a system which is emulsified by amine oxide emulsifiers.

The invention claimed is:

1. A method of controlling the proliferation of fungi in a water-in-oil emulsion which comprises incorporating into said emulsion as a fungicidal agent a condensation product and an amine oxide as an emulsifier, said condensation product being formed by mixing 1,4-dihalo-2-butene and 1,4-bis-dimethylamino-2-butene dissolved in a solvent at room temperature whereby an exothermic reaction is obtained causing the temperature of the mixture to rise, then maintaining the mixture at no higher than reflux temperature until the reaction is complete, the reactants being present in the reaction in relative molar proportions to each other of between about 1:3 and about 3:1, said condensation product being present in the emulsion in a fungicidally effective amount, and said amine oxide being present in an amount to effectively emulsify the composition.

2. The method of claim 1 wherein said amine oxide is a higher alkyl dimethylamine oxide.

3. The method of claim 1 wherein said amine oxide is stearyldimethylamine-N-oxide.

* * * * *